United States Patent [19]

Goldberg

[11] 4,169,014

[45] * Sep. 25, 1979

[54] METHOD OF IMMOBILIZING PROTEINACEOUS SUBSTANCES

[75] Inventor: Bruce S. Goldberg, Clifton, N.J.

[73] Assignee: Amerace Corporation, New York, N.Y.

[ * ] Notice: The portion of the term of this patent subsequent to Jul. 25, 1995, has been disclaimed.

[21] Appl. No.: 893,009

[22] Filed: Apr. 3, 1978

Related U.S. Application Data

[60] Division of Ser. No. 714,291, Aug. 16, 1976, Pat. No. 4,102,746, which is a continuation-in-part of Ser. No. 609,077, Aug. 29, 1975, abandoned.

[51] Int. Cl.$^2$ .............................................. C07G 7/02
[52] U.S. Cl. ................................ 435/182; 260/112 R
[58] Field of Search ................... 195/68, 63, DIG. 11; 260/2.5 R, 112 R, 6; 264/49; 210/65

[56] References Cited

U.S. PATENT DOCUMENTS

| | | | |
|---|---|---|---|
| 3,766,013 | 10/1973 | Forgione et al. | 195/63 |
| 3,791,927 | 2/1974 | Forgione et al. | 195/63 |
| 3,862,030 | 1/1975 | Goldberg | 210/65 X |

FOREIGN PATENT DOCUMENTS 954202 4/1964 United Kingdom .

OTHER PUBLICATIONS

Wheeler, et al., Some Properties of Two Phosphatases Attached to Insoluble Cellulose Matrices, Biochim. Biophys. Acta, vol. 191, 1969, (pp. 187–189).

Thang, et al., Observations on the Activity of Enzymes after Filtration (and through) a Nitrocellulose Membrane, Biochem. and Biophys., Res. Comm., vol. 31, No. 1, 1968 (pp. 1–8).

*Primary Examiner*—David M. Naff
*Attorney, Agent, or Firm*—S. Michael Bender; Richard A. Craig

[57] ABSTRACT

Proteins such as enzymes are immobilized on a microporous member comprising a binder or matrix and finely divided filler particles dispersed throughout the binder. The proteins are coupled to the filler particles, and the microporous member has a relatively large surface area and a large number of available protein coupling sites. Enzymes coupled to the microporous member have a relatively high reaction efficiency when used to act on a substrate.

16 Claims, No Drawings

METHOD OF IMMOBILIZING PROTEINACEOUS SUBSTANCES

This is a division of application Ser. No. 714,291, filed Aug. 16, 1976, now U.S. Pat. No. 4,102,746, which is a continuation-in-part of application Ser. No. 609,077, filed Aug. 29, 1975, now abandoned.

The present invention relates generally to enzyme systems, and more particularly, to method and means for immobilizing enzymes by coupling or bonding same to an insoluble support or carrier.

As is well documented in the art, enzymes are proteinaceous substances generally of high molecular weight, which function as biological catalysts capable of promoting a wide range of chemical reactions, e.g., reacting glucose with the enzyme glucose isomerase to produce fructose. Unfortunately, most enzymes are soluble in water making it difficult to remove them from solution for repeated use and/or maintain their catalytic effectiveness over an extended period of time. In addition, enzymes are frequently relatively expensive to obtain or produce in commercial quantities. Accordingly, many techniques have been proposed heretofore to immobilize enzymes and render them insoluble typically by bonding or coupling them to an insoluble support or carrier. As used herein, the terms "immobile" or "immobilized" when applied to enzymes, refer to enzymes which have been made essentially water-insoluble through attachment to, or entrapment within, a water-insoluble carrier in such a manner that they retain their activity, can readily be removed from a reactive solution, and can be repeatedly used.

Prior attempts to carry out catalytic reactions employing immobilized enzymes have met with more or less success depending in part upon the method of coupling or bonding the enzymes to the insoluble carrier; the nature or physical and chemical properties of the carrier material itself; and the mass transfer mechanism under which a substrate is brought into contact with the enzyme carrier. The term "substrate" as used herein means a substance upon which an enzyme reacts catalytically.

For example, enzymes have been adsorbed to siliceous carriers such as porous glass beads (U.S. Pat. No. 3,556,945) or have been chemically coupled to such porous beads by an intermediate silane coupling agent (U.S. Pat. No. 3,519,538). Porous ceramic beads have been suggested in lieu of glass with the enzyme being coupled via adsorption (U.S. Pat. No. 3,850,751). However, because the aforementioned porous glass or ceramic beads are extremely small in size it is necessary in order to effect the enzymatic reaction to cause the substrate to flow through a packed bed of many such discrete particles. Packed bed enzyme reactors are expensive, susceptible to clogging or channeling, present a relatively high resistance to flow, and tend to retain the substrate within the pores due to the latter's relatively small size thus presenting a contamination problem when a series of different substrates or samples are fed through the packed bed and the enzyme reaction is a relatively fast one.

Similarly, as further reported in the literature (U.S. Pat. No. 3,824,150) enzymes have been immobilized by mechanical entrapment within a semi-permeable carrier such as a membrane, or by chemical coupling through an intermediate agent to natural or synthetic polymeric materials including cellulosic materials in the form of filter paper. In the membrane or mechanical entrapment reactor, the enzymatic reaction can take place only by diffusion of the substrate solution through the support, and furthermore, the use of such supports often do not impart any extra stability to the enzyme. The use of cellulosic filter paper and similar organic carriers having enzymes coupled or otherwise bonded thereto suffer from disadvantages inherent in such support materials inasmuch as the latter usually are fragile, are subject to chemical and microbial attack, and cannot be easily sterilized without damage.

Still further, it is known to apply a water insoluble polymeric coating having nitrilo, acid amido, or ureido groups to a single phase macroporous polymeric support and then couple enzymes by adsorbtion to the coated surface of such support (U.S. Pat. No. 3,705,084). The preparation of such coated reactors, however, is time consuming and expensive; and the amount of enzymes which may be attached to a unit volume of the resulting reactor is somewhat limited by the fact that the support material is macroporous.

Against the foregoing background, it is a primary objective of the present invention to provide an improved immobilized enzyme system and method for preparing same.

It is another objective of the present invention to provide an immobilized enzyme system comprising an enzyme coupled or bonded to an insoluble, fluid permeable support or carrier in the form of a microporous member that is non-biodegradable and resistant to chemical attack; has a large surface area, high permeability, excellent physical strength characteristics; can easily be sterilized; and which is relatively inexpensive to fabricate.

It is still another objective of the present invention to provide method and means for chemically bonding an enzyme to an insoluble, fluid permeable microporous support member whereby an improved immobilized enzyme system may be produced.

It is still another objective of the present invention to provide means for carrying out a chemical process by enzymatically reacting a substrate with an enzyme coupled to an insoluble fluid permeable microporous member.

Toward the accomplishment of the foregoing objectives and advantages, the present invention, briefly summarized, contemplates the provision of an insoluble microporous member comprising a polymeric matrix or binder and particles of filler material dispersed throughout the matrix. The microporous member is treated in such a manner as to bond or couple enzymes to the filler particles dispersed throughout the matrix. The resulting immobilized enzyme composite may then be placed in contact with a substrate to carry out an enzymatic reaction.

Additional objects and advantages as well as a more complete understanding of the invention will be made more apparent from a study of the following detailed explanation thereof.

In accordance with the present invention, it has been found that an improved immobilized enzyme system may be produced by coupling or bonding an enzyme to an insoluble support or carrier in the form of a stable, inert, three-dimensional fluid permeable member comprising a binder, finely divided filler particles dispersed throughout the binder in a fixed or dimensionally stable manner, and which includes a pervasive network of substantially interconnected micropores surrounding and including said filler particles.

An example of a microporous material of the foregoing type and one which is especially suitable and therefore particularly preferred for use as an insoluble enzyme carrier or support in accordance with the present invention is fully described in U.S. Pat. No. 3,862,030, which is hereby incorporated herein by this reference and made part of this disclosure. As is evident from the U.S. Pat. No. 3,862,030, such microporous material comprises a normally hydrophobic polymeric matrix (e.g., polyvinyl chloride), finely divided normally hydrophilic filler particles (e.g., silica) dispersed throughout the resinous matrix, and a network of interconnected micropores formed throughout the material. The network of interconnected micropores, in turn, consists of micropores formed between adjacent or neighboring particles of the dispersed inorganic filler, between particles of dispersed filler and the resinous matrix, and in the resinous matrix itself, with the size distribution of the micropores typically ranging over a relatively broad range from about 0.01 micron to about 100 micron, and the mean pore diameter of the micropores typically being in the range of about 0.1 micron to about 0.2 micron as determined, porosimetrically by the Mercury Intrusion Method. Furthermore, the total porosity of such material is typically within the range of about 50% to about 70%. Such microporous materials have been employed heretofore, for example, in the fabrication of battery separators as disclosed in U.S. Pat. No. 3,696,061, or more recently, as sub-micron filter media as disclosed in the aforementioned U.S. Pat. No. 3,862,030.

It will be appreciated that microporous materials other than those disclosed in the U.S. Pat. No. 3,862,030 may also be used in practicing the present invention. Thus, for example, in lieu of the thermoplastic binder constituent of the microporous material of the U.S. Pat. No. 3,862,030, synthetic or natural thermosetting rubber polymers or copolymers thereof may be employed.

If formed of rubber-like polymers, the latter, with additives such as antidegradants, cross-linking agents, inert fillers, or the like normally employed by those skilled in the art of compounding thermosetting compounds, are intimately mixed using conventional methods with a suitable filler, such as silica hydrogel or precipitated hydrated silica (i.e., silicic acid (n $SiO_2$ m $H_2O$) where n and m are integers) the latter being available commercially, for example, under the trademark Hi-Sil from PPG Industries. The resultant compound is then formed into a sheet, preferably by calendering onto a suitable carrier (i.e., paper or a thin metal sheet or screen), wound on reels of convenient size, and then vulcanized under hydrostatic conditions in a steam autoclave to an appropriate state of cure using pressurized steam as the source of heat. The vulcanized sheet is then dried in a warm dry air stream which also serves to dehydrate the silica. Such dehydration results in the formation of micropores in the sheet caused by the shrinkage of the silica thereby forming a normally hydrophilic microporous article.

In the finished state a typical thermoset rubber-like polymeric based microporous sheet contains about 1 part of rubber-like polymer to about 0.5 parts silica by weight, and is about 60 percent porous on a volume basis. The pore size distribution is typically rather wide, varying from about 0.05 to 10 microns for the most part according to mercury intrusion data, the mean pore size being typically about 1.4 micron. Such thermoset rubber-like polymeric sheets are normally hydrophilic and liquid water soaks rapidly into the material, passing through without any applied pressure, indicating that the micropores are substantially interconnected. Such sheets, and the process of making same, are known in the prior art.

In broad aspect, the present invention contemplates utilization of the finely divided filler particles dispersed throughout the binder or matrix of the microporous material as active sites to which enzymes may be coupled. Due to its porous construction and the dispersion of the filler particles throughout the matrix or binder, such microporous material has a relatively large surface area, typically on the order of about 80 $M^2/g$, and the number of available enzyme coupling sites is relatively large; hence, the loading factor or amount of enzymes which may be coupled per unit volume of such microporous material has been found to be correspondingly large. In addition, since each filler particle is in effect surrounded by the interconnected network of varying sized micropores, a substrate in the form of a fluid or aqueous stream flowing through, for example, a relatively thin sheet of microporous material having enzymes coupled thereto will immediately come into contact with or gain access to a great many enzyme sites thus promoting extremely rapid enzymatic reactions with high product conversion efficiency. Thus, if the reaction efficiency of the enzyme is relatively high, the sheet may be made quite thin and essentially complete reactions effected almost instantaneously upon passage of the substrate therethrough. By the same token, less efficiently reactive enzymes may necessitate slightly thicker sheets, and slightly longer reaction times to effect essentially complete product conversions. Owing to its high degree of porosity and the hydrophillic nature of its dispersed filler constituent, the microporous material wets easily and is quite permeable to fluids flowing therethrough. Thus, relatively low hydraulic pressures are required to pass a substrate through the material. For example, as pointed out in the aforementioned U.S. Pat. No. 3,862,030, flow through rates ranging from about 0.4 gallons/min./sq. ft. to about 9 gallons/min./sq. ft. have been achieved through sheets of the preferred microporous material having a thickness of about 0.02 inches under a pressure gradient of only 10 psig, and having filler/binder ratios in the range from about 1/1 to about 2/1. Generally, an increase in the filler to binder ratio will result in increased pore size and greater total porosity thereby resulting in an increase in permeability of the material. Accordingly, the immobilized enzyme support of the present invention is particularly suitable for use in the form of a so-called flow-through reactor core, that is, a reactor core wherein the substrate solution penetrates one surface of the enzyme laden material, is catalytically reacted upon the enzyme, and the converted product as well as any unreacted substrate exit through the same or another surface of the material.

Moreover, since as mentioned above, the pore size distribution of the microporous support material extends over a relatively wide range (i.e., about 0.01 micron to about 100 micron) and the micropores are substantially interconnected, the material contains a multitude of sufficiently sized paths along which both substrate and/or converted product may easily flow. Product efflux from the material is thus quite rapid and may be terminated substantially simultaneously with end point flow of the substrate through the support material. In other words, catalytic reactions produced with the enzyme support contemplated by the present invention have an extremely sharp cutoff, and accordingly, many different substrate samples may be fed through the same immobilized enzyme support in rapid succession without the danger of contamination between successive samples, an extremely desirable advantage when immobilized enzymes are employed to carry out successive catalytic reactions on a series of different substrate samples as in medical or industrial analytical instruments, for example.

The foregoing constitutes a significant advantage of the present invention since in other known immobilized enzyme reactors such as the packed bed of porous glass beads, or the membrane reactor, for example, pore size is controlled quite uniformly and is of such small size that mass transfer through the reactor is accomplished by diffusion. In such diffusion limited enzyme reactors, total efflux time of the product may lag significantly behind the substrate sample termination point, thus presenting a contamination problem should a succeeding substrate sample be fed into the reactor too rapidly.

In addition to the foregoing advantages, the microporous enzyme support material of the present invention has excellent strength characteristics typically having a tensile strength of about 400 psi and a percentage of elongation under 20%, and thus may be handled quite easily during the various stages of treatment necessary to bond or attach enzymes thereto as will be explained in more detail below. Moreover, due to its excellent dimensional stability and strength, the microporous material of the present invention resists compaction under hydraulic pressures, and therefore is especially adapted to be employed in large scale bulk processing reactors where large enzyme reaction areas are involved and large dynamic forces are exerted on the enzyme support member such as, for example, in commercial industrial or chemical processes utilizing enzymatic reactions. Moreover, the preferred microporous material is resistant to attack by chemicals such as acids and alcohols, for example, and is capable of being exposed to elevated temperatures without affecting its physical properties. In regard to the latter, it has been found possible, for example, to heat sterilize the preferred microporous material by emersion in steam at 15 psi and 240° F. for 30 minutes without degrading the dimensional stability or physical properties of the material.

As more fully disclosed in the aforementioned U.S. Pat. No. 3,862,030, the particularly preferred microporous material may be fabricated by admixing suitable quantities of a finely divided polymeric resin, a finely divided inorganic filler, a solvent (e.g., cyclohexanone) and a non-solvent (e.g., water) under low shear conditions to form a stable, damp, free-flowing powder. The powder mixture may then be extruded and calendered preferably to form a substantially planar structure or sheet of desired dimensions which may next be passed through an aqueous bath to leach out the solvent, and then subsequently passed through a heated air-oven to remove all traces of moisture. In accordance with the present invention, the resulting article in the form of a microporous, dimensionally stable, semi-rigid, insoluble, fluid permeable member may then be treated in such a manner as to couple or bond enzymes thereto.

As is generally known in the art, it is possible to bond or attach enzymes to an insoluble support or carrier by directly adsorbing the enzyme on the carrier, or by indirectly adsorbing or covalently bonding the enzyme to the carrier through an intermediate coupling agent. Due primarily to its dispersed silica filler component, the preferred microporous support material of the present invention has been found to exhibit a net negative charge as evidenced by substantial adsorption of proteins thereto at pH values below the isoelectric point of the adsorbed protein. Thus, although direct adsorption of enzymes to the dispersed filler particles in the material is feasible, the adsorptive interaction (direct) has been found to be of insufficient magnitude to prevent relatively rapid desorption during use and subsequently, loss of enzymatic activity from the enzyme composite.

Accordingly, in carrying out the present invention, it is preferred that the microporous material be treated in such a manner as to effect a chemical bond between the catalytically active enzyme and the insoluble microporous support material. In its untreated condition, the microporous material lacks the organic functionality necessary to effect such chemical bonding to proteinaceous substances, hence, any known technique for imparting the required functionality to the microporous material may be employed since the present invention in its broadest aspect is concerned with the discovery that the bonding of enzymes to the microporous starting material results in a superior immobilized enzyme composite. Most known enzymes may be immobilized by covalently coupling or cross-linking free amino residues or groups on the enzyme molecule which are not essential to the enzymatic activity of the enzyme to a carrier surface containing aliphatic primary or secondary amino or hydroxyl groups or residues. Still other known enzymes may be covalently coupled or cross-linked to a carrier surface in similar fashion via such other functional groups as, carboxyl, isonitrile, aldehyde or ketone, or anion, to name a few. Therefore, it will be understood that the term "chemical bond" or "chemically bound" as used therein and in the appended claims refers broadly to the chemical linkage between the catalytically active protein or enzyme and the functional groups or residues imparted to the microporous starting material and is not to be construed as being limited to a particular functional group or residue or to a particular enzyme.

In one preferred embodiment of the present invention, aliphatic primary amine functionality may be imparted to the microporous starting material by covalently bonding directly to the dispersed filler particles in the microporous material a bridging agent in the form of an organosilane such as gamma-aminopropyltriethoxysilane, whereas in another alternatively preferred embodiment of the invention aliphatic primary amine functionality may be imparted to the microporous material by irreversibly chemiadsorbing directly to the dispersed filler particles in the microporous material a bridging agent in the form of a macromolecular polyelectrolyte such as polyethylenemine (PEI). Enzymes may then be covalently bonded or cross-linked to the chemically modified microporous material and more specifically to the aliphatic primary amine residues imparted to the surface of the material by the aforementioned bridging agents.

In the case where a bridging agent such as gamma-aminopropyltriethoxysilane is employed, the latter is believed to be primarily covalently bonded directly to the hydrophilic inorganic filler particles dispersed through the polymeric binder constituent of the microporous material. Generally speaking the use of a silane bridging agent to bond or attach enzymes to siliceous materials is known in the art as disclosed, for example, in the aforementioned U.S. Pat. No. 3,519,538, which is hereby incorporated herein by this reference.

In the case where a bridging agent such as polyethylenemine is employed, the latter is believed to be attached or bonded to the dispersed hydrophilic inorganic filler constituents of the microporous material via strong chemiadsorptive forces. Generally, the use of a macromolecular polyelectrolyte or polyamine as a bridging agent to bond or attach enzymes to the surface of colloidal particles of silica, or to fibrous cellulose, is known in the art as respectively disclosed, for example, in U.S. Pat. Nos. 3,796,634 and 3,741,871, each of which is also incorporated herein by this reference.

In both cases, the enzyme is preferably cross-linked to the bridging agent by means of a bifunctional electrophilic reagent such as glutaraldehyde or bisimidate esters to effect the desired covalent conjugation of the enzyme to the functional amine groups which have been imparted to the external surfaces of the hydrophilic filler particles dispersed throughout the microporous carrier or support via the bridging agent.

When using a carrier surface adsorptive bridging agent in the form of the aforementioned polyethylenimine, for example, or a bridging agent covalently bonded to the carrier surface such as the aforementioned gamma-aminopropyltriethoxysilane, for example, covalent conjugation of the enzyme and the carrier may be carried out in a single or two step procedure. In the single step procedure, the chemically modified carrier material may be simultaneously treated with the bifunctional electrophilic reagent and the enzyme to effect simultaneous intermolecular cross-linking of the carrier surface reactive polymer and the enzyme. Commercial grades of glutaraldehyde, a typical bifunctional reagent as mentioned above, contain significant amounts of soluble polymeric compounds formed from intermolecular aldol condensations of the monomeric dialdehyde, hence, each site of condensation results in a highly reactive alpha-beta unsaturated aldehyde moiety which will rapidly undergo Michael type addition reactions involving nucleophiles such as aliphatic amines or other residues found on the surface of enzymes. In addition, free aliphatic aldehyde groups which are present in the carrier surface reactive polymer may also participate in the cross-linking reactions by combination with aliphatic amino residues of the carrier or enzyme to form Schiff bases. Although the degree to which desired covalent conjugation of the enzyme competes with such undesired, unproductive reactions resulting in simple protein modification and cross-linking of carrier reactive surface residues may be empirically determined by varying experimental conditions such as pH, protein concentration and cross-linking reagent concentration, it is difficult to selectively control such undesired, competitive reactions as the bifunctional cross-linking reagent is always present in a substantial molar excess during the reaction. In certain cases, therefore, employment of the single step procedure may result in partial or total enzyme inactivation due to extensive chemical modification of the enzyme or to chemical modification of the essential active site residues.

In situations where chemical modification results in extensive enzyme inactivation, the two step procedure is recommended wherein the chemically modified carrier material is first cross-linked with the bifunctional reagent and then subsequently incubated with the enzyme. By using a suitably high concentration of the cross-linking reagent, bimolecular reactions can become competitive for the surface amino residues relative to intramolecular processes such as cross-linking. This results in a high surface density of pendant residues capable of reacting with nucleophilic side chain residues of enzymes. After removal of the excess unreacted cross-linking reagent, the enzyme of interest may then be incubated with the modified carrier resulting in covalent conjugation of the enzyme and the carrier. The foregoing two step procedure has been found to result in minimal modification of the enzyme since only residues in the vicinity of the contact region between the enzyme and the carrier reactive surface are involved.

It will be appreciated that various chemistries other than the electrophilic bifunctional reagents mentioned above can be employed to covalently bond enzymes to the chemically modified carrier material. Such alternatives may include, for example, acylation of the aliphatic amino group at the carrier reactive surface with succinic anhydride to produce a pendant aliphatic carboxyl group which is subsequently reacted with nucleophilic side chain residues of enzymes in the presence of a water soluble carbodiimide; direct reaction of the amino group at the carrier reactive surface with side chain carboxyl groups of enzymes in the presence of a water soluble carbodiimide; acylation of the amino group at the carrier reactive surface with p-nitrobenzoyl chloride, reduction of the aryl nitro to an aryl amine via sodium dithionite, oxidation of the aryl amino group to an aryl diazonium salt via nitrous acid and subsequent reaction with aromatic side chain residues of proteins to form a stable azo linkage; acylation of the amino group at the carrier reactive surface with terepthaloyl chloride, reaction of the pendant p-benzoyl acid halide with hydrazide to a benzoyl azide and subsequent reaction with nucleophilic side chain residues of enzymes.

When reacting the enzyme with the chemically modified carrier, the enzyme is preferably placed in a buffering solution and the reaction carried out at temperatures sufficiently low to avoid deactivation of the enzyme or substantial changes in the latter's conformational state. Generally, temperatures in the range of about 5° C. to about 50° C. are acceptable. As is known in the art, the pH of the enzyme reaction solution may be controlled at a desired level, by selecting suitable buffers, depending upon the particular enzyme being bound. Likewise, the concentration of enzyme in the buffered reactive solution and therefore, the extent to which the chemically modified carrier will be loaded with enzymes may be chosen depending upon the conversion rate of the enzyme, the concentration of the substrate, and the flow rate of the substrate through the reactor core.

The present invention now will be further described with reference to the following examples thereof, which latter are intended for illustration purposes only and are not to be construed as limiting the scope of the invention.

EXAMPLE 1

PREPARATION OF UNTREATED ENZYME SUPPORT MEMBER

A sheet of microporous material was prepared by first dry blending 20.0 lbs. of Conoco 5385 polyvinyl chloride resin having a particle size of about 80 mesh, and 40.0 lbs. of Hi Sil 233, a precipitated hydrated silica, in a Patterson Kelley "low shear" liquids-solids blender for approximately 3 minutes. Thereafter, and during continued agitation, 54.6 lbs. of solvent (cylohexanone) were added over a 20 minute period by means of a pump. Water in an amount of 59.0 lbs. was then added to the mix in the agitating blender over a subsequent 20-minute period to form a damp, stable, free-flowing powder. The powder was then introduced into a screw extruder having a barrel temperature of approximately 120° F., and the extrudate passed between the rolls of a calender to obtain a substantially flat sheet having a thickness of 0.02 inches (0.5mm). The sheet was then passed through an extraction bath of water at 170° F., and subsequently dried in a hot air oven at 225° F., for 6 minutes. The finished microporous sheet had a relatively wide pore size distribution extending from about 0.01 micron to about 100 micron, and a mean pore diameter in the range of about 0.15 micron to about 0.25 micron as determined by the Mercury Intrusion Method. In addition, the total porosity of this material is approximately 65% by volume and the dispersed filler content (e.g., silica) comprises approximately 56% by weight. Liquid water soaked rapidly into the material without any applied pressure indicating that the micropores are substantially interconnected from surface to surface. From the resulting substantially flattened, semi-rigid, microporous sheet a plurality of untreated support members 5×5cm in size were cut and heat sterilized by immersion in a steam bath for one hour and allowed to cool and dry in open air.

EXAMPLE 2

CHEMICAL MODIFICATION BY COVALENT BONDING

An untreated support member prepared in accordance with Example 1 was incubated in a 10% vol/vol aqueous solution of gamma-aminopropyltriethoxysilane containing 1% vol/vol concentrated HCl for 24 hours. The treated support member was flushed with water and 1 M NaCl to remove all unreacted reagents. The presence of aliphatic primary amino residues was then qualitatively assessed by reacting the treated member with 0.5% wt/vol trinitrobenzene sulfonic acid in 0.1 M sodium tetraborate buffer at 70° F. and observing an intense orange trinitrophenyl amine derivative on the surface of the treated support member. Another untreated support member prepared in accordance with Example 1 was similarly asseyed, but displayed no reaction to this test. Elemental analysis of the treated support member yielded 0.5% nitrogen by dry weight above that of the untreated support member. The permanence of the amino functionality on the treated support member was evidenced by negligible nitrogen loss after storage in water for a period of 12 months. The treated support member displayed identical flow properties with respect to the untreated support member and was not sensitive to differences in the buffers or ionic strength.

EXAMPLE 3

CHEMICAL MODIFICATION BY CHEMIADSORPTION

Another untreated support member prepared in accordance with Example 1 was incubated in a 5% wt/vol aqueous solution of 50,000 mol. wt. branched chain polyethyleneimine (PEI) at room temperature for one hour. The treated support was flushed with water and 1 M NaCl to remove any unadsorbed PEI. Assey was by the same trinitrobenzene sulfonic acid test employed in Example 2 and an intense orange trinitrophenyl amine derivative was observed on the surface of the treated support member demonstrating substantial aliphatic amino functionality. The nitrogen loading on the treated support member was quantitated by elemental analysis and was 1.25% nitrogen by dry weight versus 0.02% nitrogen by dry weight of an untreated support member. The chemiadsorption of PEI on the treated support member appeared virtually irreversible since it could not be removed by incubation with high ionic strength solutions (e.g., 1 M NaCl or 1 M $K_2HPO_4/KH_2PO_4$) at pH values between 3 and 9. Only in the case of strong acidic conditions (incubation in 1 M HCl for 2 hours) was there evidence of partial desorption amounting to 50% of the nitrogen content as indicated by elemental analysis. The surface area of the treated support by standard BET procedure was 55.4 $M^2/g$ versus 81.1 $M^2/g$ for the control. The support member treated with PEI displayed identical flow properties compared to an untreated support member irrespective of the buffer or ionic strength used.

EXAMPLE 4

ENZYME COUPLING REACTION (Glucose Oxidase)

The support member treated in accordance with Example 3 was incubated for one hour in 10% vol/vol aqueous solution of glutaraldehyde at pH 7. The support member was then rinsed with water and incubated for one hour in a solution of glucose oxidase which had been purified to homogeneity from *Aspergillis niger*. The conditions of the enzyme coupling reaction were as follows: glucose oxidase concentration 20 mg/ml in 0.1 M $K_2HPO_4/KH_2PO_4$ buffer pH 6.0 at ambient room temperature. Directly pumping the enzyme solution through the support member under a positive hydraulic pressure did not improve enzyme loading relative to that obtained by simple incubation. The temperature of the coupling reaction was not found to be critical with the only requirement being that it did not exceed the thermal inactivation region of 50° C. for glucose oxidase. The support member was then extensively washed with water and 1 M NaCl to remove unreacted enzyme. Quenching of electrophilic residues on the support member surface was achieved by incubation of the immobilized enzyme composite with 0.1 M ethanolamine at pH 7.0 containing 50 mM $NaCNBH_3$. The immobilized enzyme appears to have an indefinite shelf life when stored at 4° C. in 0.1 M $K_2HPO_4$ buffer pH 6.0.

EXAMPLE 5

SINGLE ENZYME REACTOR

The following reaction was carried out employing a pair of 1.5 cm diameter disks prepared in accordance with Example 4 and mounted in a stacked configuration in a flow-thru reactor wherein the flow vector of the substrate was substantially perpendicular to the plane of each disk. The cross section of each mounted disk exposed to the fluid stream was 79 mm². Glucose oxidase (E.C.1.1.3.4.) catalyzes the aerobic oxidation of glucose $$\beta\text{-D-glucose} + O_2 \rightarrow \text{D-gluconolactone} + H_2O_2$$

Enzymatic activity in the stacked disk reactor configuration was evaluated by measuring oxygen depletion downstream from the reactor with a Biological Oxygen Monitor, Model No. 53, obtained from Yellow Springs Instrument Company. A solution of 0.15 mM glucose at anomeric equilibrium in air saturated 0.1 M Na acetate buffer pH 5.5 was pumped through the reactor at a flow rate of 2 ml/min. The conversion of the limiting substrate, β-D-glucose, was quantitative as measured by oxygen depletion downstream from the reactor. The residence time of the sample stream in contact with the reactor was approximately 1.6 seconds. The integrated form of the rate equation for glucose oxidase under these experimental conditions is known explicitly, and it can be calculated that the lower limit for the immobilized enzyme concentration is 10 mg/ml. The unusually high activity of the stacked disk reactor is attributed to the absence of internal mass transport effects, i.e., no evidence of internal mass transport constraints for the reactor was observed.

A second set of stacked disks were prepared in accordance with Example 4 and mounted in the flow-thru reactor; the disks, however, were prepared with substantially reduced concentration of the immobilized enzyme, i.e., by a factor of 10. A 1 mM glucose solution in 0.1 M Na acetate buffer pH 5.5 was then pumped through the second disk reactor at flow rates sufficiently fast that the reactor was operating in a kinetic mode with only partial conversion of glucose to gluconolactone. The steady-state level of substrate conversion by the reactor under this condition was found to be highly sensitive to the enzyme concentration. When observed under continuous operation for a period of four hours, no change in the steady-state conversion level was observed indicating no loss of enzymatic activity from the reactor.

EXAMPLE 6

ENZYME COUPLING REACTION (Alcohol Dehydrogenase)

Another support member treated in accordance with Example 3 was incubated for one hour in a 10% vol/vol aqueous solution of glutaraldehyde at pH 7. The support member was then rinsed with water and incubated for one hour in a solution of alcohol dehydrogenase. The conditions of the enzyme coupling reaction were as follows: alcohol dehydrogenase concentration 5 mg/ml in 0.1 M K$_2$HPO$_4$KH$_2$PO$_4$ buffer pH 6.0 containing 0.1 mM EDTA and 10 μM NADH (reduced nicotinamide adenine dinucleotide) at ambient room temperature. The support member was then extensively washed with the reaction buffer and 1 M NaCl to remove unreacted enzyme. Unreacted electrophilic residues on the support member were quenched by incubation of the immobilized enzyme composite with 0.1 M ethanolamine at pH 7.0 containing 50 mM NaCNBH$_3$. The enzyme loading was 11 mg/g of the carrier and was calculated by measuring the incremental increase in nitrogen upon the support member prior to the quenching reaction.

Alcohol dehydrogenase (EC 1.1.1.1) catalyzes the reversible oxidation of primary alcohols according to the equation

Enzymatic activity in a stacked disk reactor configuration was evaluated by measuring spectrophotometrically the formation of NADH @340 nm downstream from the reactor with a flow-through Model UA-5 absorbance monitor obtained from Instrumentation Specialties Co. A single 1.5 cm disk of the immobilized enzyme was mounted into a flow-through reactor in the manner of Example 5. A solution of 50 mM ethanol and 0.5 nM NAD⊕ in 0.1 M K$_2$HPO$_4$/KH$_2$PO$_4$ buffer pH 7.4 containing 10 μM EDTA was pumped through the reactor at a flow rate of 1 ml/min. The calculated equilibrium conversion for the reaction under these conditions is 16% of the starting NAD⊕ concentration. Complete equilibration was observed indicating that a few milliseconds contact with the immobilized enzyme reactor were sufficient to achieve the thermodynamic limit of the reaction. In order to demonstrate the stability of the immobilized enzyme a set of conditions was chosen in which the reactor was operated for 24 hours in a kinetic mode. As the conversion of substrates to products is extremely sensitive to conservation of the catalyst under these conditions, a decrease in the conversion level indicates loss or inactivation of the enzyme. The conditions of the experiment were 5 mM ethanol and 50μM NAD+ in 0.1 M K$_2$HPO$_4$/KH$_2$PO$_4$ buffer pH 7.0 containing 10μM EDTA. This solution was pumped through the reactor at a flow rate of 1 ml/min for 24 hours with continuous monitoring and recording of the substrate conversion level. It was found that the conversion remained constant during this period indicating complete conservation of the immobilized enzyme.

EXAMPLE 7

TANDEM ENZYME REACTOR

A disk reactor system incorporating three different immobilized enzyme composites was constructed for catalyzing the reaction sequence shown below.

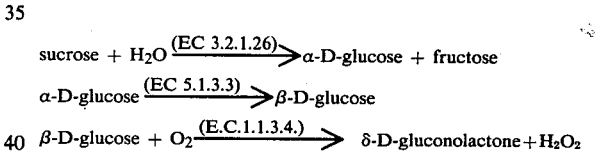

The glucose oxidase was homogeneous and prepared from *Aspergillis niger*, the aldose-1-epimerase enzyme (EC 5.1.3.3) was prepared from hog kidney and was 20% wt/wt purity, and the α-D-fructofuranosidase (EC 3.2.1.26) was a high purity preparation from *Candida utilis*. Each of the aforementioned enzymes was covalently immobilized to a pair of 1.5 cm disks in accordance with the method of Example 4 at an enzyme concentration of 20 mg/ml. The aldehyde quenching reaction was not employed. The two sets of three disks, each disk in each set corresponding to one of the three enzymes in the coupled reaction and in the sequence shown above, were then mounted in the flow-thru reactor of Example 5 in a stacked fashion. A 1 mM solution of ultrapure sucrose in 0.05 M K$_2$HPO$_4$ pH 6.0, air saturated at 25° C. was then pumped through the reactor at a flow rate of 1.2 ml/min. The conversion as measured by oxygen depletion downstream from the reactor was 10% the theoretical based upon the known stoichiometry of the overall reaction. The maximum conversion which could be obtained, however, was 25% since dissolved oxygen is the limiting substrate (250μM). Under the conditions employed for this example, the aldose-1-epimerase is the rate limiting enzyme. At slower flow rates and consequently longer reactor residence times, measured conversions approaching 25% were obtained.

EXAMPLE 8

IMMOBILIZATION OF GLUCOSE ISOMERASE ON MICROPOROUS CARRIER

Glucose isomerace (E.C. 5.3.1.5) catalyzes the reversible interconversion of β-D-fructose to α-D-glucose in accordance with the following reaction:

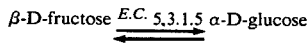

Four discs of 26 mm diameter were cut from a sheet of microporous material (Example 1) and treated in accordance with Example 3 and then mounted in stacked fashion into a standard Millipore filter holder without gasket seals to form a flow-thru reactor. The PEI laden support discs were modified by pumping glutaraldehyde (10% wt/vol pH adjusted to 8.0) through the reactor in a recycled mode from a 100 ml reservoir for 1 hour. The support member was then rinsed in-situ by pumping 500 ml (approximately ½ hour) of deionized water and 200 ml of Hepes buffer or equivalent (i.e. 2g/l Mg SO$_4$.7H$_2$O and 0.2g/l CoSO$_4$.7H$_2$O pH 7.0–7.5 in deionized water) through the reactor. A solution of glucose isomerase at pH 7.5 (30 ml containing 0.43 units/ml) was passed through a Millipore 0.65 micron filter and circulated through the disc reactor for 1 hour at room temperature. The term "units" as used herein refers to units of activity and is defined as that amount of enzyme which catalyzes the conversion of 1 micromole of β-D-fructose to α-D-glucose per minute at 25° C. The reactor was rinsed with approximately 500 ml of Hepes buffer until no protein could be detected in the effluent. The glucose isomerase enzyme immobilized in this Example was obtained as a lyophilized whole cell homogenate of *Streptomyces albus* from Novo Enzyme Corporation and purified by soluble protein isolation and fractionation with ammonioum sulfate (AmSO$_4$). Although the fractionation depends in part upon the initial protein concentration of the supernatant obtained from the protein isolation step, the major glucose activity is typically found in the 70–85% AmSO$_4$ pellet. The protein pellets containing the majority of the activity are dissolved in ~20–30 ml of Hepes buffer and dialyzed against 4 liters of buffer for 24 hours at 4° C. using standard cellulose acetate dialysis tubing. Although the enzyme preparation at this point is suitable for use in immobilization if desired, the above enzyme concentrate can be purified still further by standard gel permeation techniques. Protein assay of the rinse affluent solution was carried out by employing the following reaction sequence:

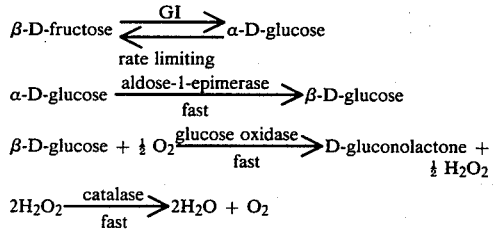

As mentioned, glucose isomerase catalyzes the reversible conversion of β-D-fructose to α-D-glucose. At 25° C. the equilibrium constant of this reaction is approximately unity and would result in an approximate 50–50 mixture of β-D-fructose and α-D-glucose. The spontaneous epimerization of the intermediate α-D-glucose to β-D-glucose is not sufficiently fast under the conditions to the assay to prevent accumulation of this intermediate and thus aldose-1-epimerase is added to the assay solution to facilitate this intermediate reaction. The reporter reaction of this analysis is the aerobic (glucose oxidase) oxidation of β-D-glucose to D-gluconolactone in the presence of catalase which results in an overall stoichiometry of two moles of β-D-fructose per mole of oxygen (O$_2$). This final reaction is monitored by means of a biological oxygen monitor such as a YSI Model 53.

The assay was carried out as follows. Into a reaction cell which was equilibrated to 25° C. 3 ml of 0.01 molar phosphate buffer, pH 8, was added and stirred at a setting of 5 on a Thomas stirrer. Then, 30 microliters of Sigma glucose oxidase Type V concentrated 10 fold and 100 microliters of aldose-1-epimerase prepared according to Lepedes and Chase[1] or equivalent was added. Subsequently, 10 microliters of Sigma-C-100 catalase (5 mg/ml concentration), and 20 microliters of 72% (4.0 molar) β-D-fructose were added to the cell. After the resulting solution had been stirred for a total of 3 to 5 minutes, the electrode of a Model 53 YSI biological oxygen monitor was carefully inserted into the cell making sure that no air bubbles were retained; such as adhering to the electrode, cell walls, or under the stir bar. With the recorder of the Model 53 YSI biological oxygen monitor operating at a chart speed of ½" per minute the trace was allowed to stabilize; that is, give a linear base line. Once a linear base line was established 100 microliters of the buffer rinse was added to the reaction cell and the recorder trace was again allowed to achieve linearity. The assay is linear up to 10 micromoles O$_2$ per minute, although slower rates are routinely employed using expanding scale attachments on the oxygen monitor. No shift in the slope of the recorder trace indicates lack of active enzyme in the buffer rinse.

[1] "Aldose-1-Epimerase from Hog Kidney: Isolation and Evidence of Purity, Chemical Studies and Inhibition Kinetics", S. L. Lapedes and A. M. Chase, *Biochem. & Biophys. Res. Comm.*, 31 967, (1968).

A loading of 0.7 units of glucose isomerase per ml of reactor matrix was calculated based upon loss of activity from the protein solution used for immobilization.

EXAMPLE 9

COMPARISON OF MICROPOROUS CARRIER WITH CONTROLLED PORE GLASS (CPG)

Controlled pore glass particles 40–80 mesh were obtained from Electronucleonics Corporation and chemically modified by standard methods[2] to introduce covalenty bound, aliphatic amino functionality on the external and internal surfaces thereof. Two grams of the amino modified CPG were degassed and suspended in 100 ml of Hepes buffer for ½ hour. The supernatant was aspirated away from the bed and the particles resuspended in 100 ml of 10% aqueous glutaraldehyde solution for 1 hour. The CPG particles were extensively washed by suspension and decantation until the odor of glutaraldehyde was gone. Ten (10) ml of the enzyme solution containing 0.43 units/ml pH 7.5 was added to the particles and allowed to react for 1 hour. A 1.2 ml volume of the particles was loaded into a small column (0.6 centimeter diameter) to form a packed bed reactor, and rinsed with the Hepes buffer until no protein could be detected in the supernatant as determined by the assay technique of Example 8. Based upon loss of activity from the reaction solution, the loading was 0.66 units/ml (CPG has a bulk density of 0.36 grams/ml) which is substantially equivalent to that of the immobilized enzyme carrier of Example 8. The relative volumes of the disc (Example 8) and packed bed reactors were within 20% being 1.0 and 1.2 ml, respectively. The reactors were empirically evaluated by measuring the degree of conversion of a 7.2% wt/vol fructose solution (0.4 molar) pH 7.0 at several flow rates in the Hepes buffer. Glucose was measured by diluting the reactor effluent 100×into 0.1 molar sodium acetate pH 5.5 and measuring the endpoint oxygen consumption in the presence of reporter enzymes. Analysis for immobilized enzyme activity was done by the same technique as used for solutions as described in Example 8 above, except that the first reaction has already been accomplished and one need only analyze for the amount of α-D-glucose in the effluent stream of the reactor. Thus the reaction:

$\beta$-D-fructose $\xrightarrow{GI}$ $\alpha$-D-glucose had already been accomplished in the reactor and is carried out with a 7.2% fructose solution in Hepes buffer. The analytical sequence of the reactor effluent is the same as equations b, c, and d of the reaction sequence of the assay technique set forth in Example 8, above.

[2]"Immobilized Enzymes: A Prototype Device for the Analysis of Glucose in Biological Fluids Employing Immobilized Glucose Oxidase", M. K. Weibel et al., *Anal. Biochem.*, 52 502 (1973).

The assay of the reactor effluent for efficiency of conversion of β-D-fructose to α-D-glucose is as follows: Into the reaction cell which was equilibrated at 25° C., 3 ml of sodium acetate buffer pH 5.5 was pipeted and stirred at a setting of 5 on the Thomas stirrer. Then, 60 microliters of glucose oxidase, 200 microliters of aldose-1-epimerase, and 10 microliters of catalase were added to the cell. After the resulting solution had been stirred for a total of 3 to 5 minutes the electrode of the YSI oxygen monitor was carefully inserted into the cell making sure that no air bubbles were retained on the surfaces of the electrode, the cell, or in the solution itself. With the YSI biological oxygen monitor recorder operating at a chart speed of ½" per minute the trace was allowed to stabilize to a constant baseline. Once a linear baseline was established, 30 microliters of reactor effluent was injected into the reaction cell and the curve was again allowed to achieve a stable slope.

The results of the empirical evaluation are tabulated below. Both immobilization and reactor studies were carried out in parallel on the same day to ensure that a direct comparison could be made. The performance of each reactor over a period of 6 hours was unchanged as determined by the constant steady state conversion of fructose to glucose when the two reactors were operated in a kinetic mode.

| Packed Bed Reactor (volume 1.2 ml) | | |
|---|---|---|
| Flow Rate | % Conversion | Residence Time |
| 1.30 ml/min | 0.38% | 0.92 min |
| 0.69 ml/min | 0.56% | 1.74 min |
| 0.20 ml/min | 1.50% | 6.00 min |
| Disc Reactor (volume 1.0 ml) | | |
| 0.75 ml/min | 0.81% | 1.33 min |
| 0.37 ml/min | 1.30% | 2.72 min |
| 0.18 ml/min | 2.45% | 5.50 min |

As can be seen from the above data, the efficiency of the packed bed reactor is consistently only 60–70% that of the stacked disc assembly when the residence times are normalized. This is quite surprising in view of calculations which indicate that the "bulk concentration" of the enzyme is for practical purposes identical for both reactors. The disc reactor was allowed to remain at room temperature in the presence of the substrate solution for 5 days. The transport characteristics of the reactor were unchanged and the percent conversion at 0.37 ml/min was slightly higher at 1.50%.

EXAMPLE 10

MICROPOROUS CARRIER HAVING THERMOSET MATRIX

In order to demonstrate that the matrix or binder constituent of the microporous enzyme carrier of the present invention is not limited to a thermoplastic polymeric resin, a sheet of microporous material was prepared by thoroughly intermixing 100 parts by weight of natural rubber, 165.5 parts of silica hydrogel, 3.1 parts inert filler (rubber dust), 39.0 parts sulfur, 0.8 parts stearic acid, and 0.8 parts diphenylguanidine in a Banbury mixer to produce a homogeneous mixture. This mixture was then extruded into sheet form and calendered to 0.047 inches thick nominal. The calendered sheet was wound on a reel and vulcanized in an autoclave for 35 minutes at 172° C. and 155 psig. The vulcanized sheet was then air-dried in an oven to remove all traces of moisture. The resulting microporous material is extremely porous having micropores which vary in size from about 0.5 micron to about 5 microns, and has a mean pore diameter of approximately 1.5 microns as determined by the Mercury Intrusion Method. In addition, the total porosity of this material is approximately 56% by volume and the dispersed filler content (e.g. silica) comprises approximately 26% by weight. Sample specimens 1.3 centimeters in diameter were punched from the finished microporous sheet on a press and utilized to form single disc reactors as follows:

1. Reactor No. 1—incubated in enzyme only
2. Reactor No. 2—incubated in polyethyleneimine, glutaraldehyde and enzyme For comparison purposes, a third single disc reactor (Reactor No. 3) was prepared by forming a disc of the material of Example 1 having a diameter of 1.3 centimeters and incubating in polyethyleneimine, glutaraldehyde, and enzyme.

Each microporous reactor disc (Reactors Nos. 2 and 3 only) having been cut to the appropriate size, was immersed in 20 cc of 5% polyethyleneimine for 30 minutes and agitated frequently to remove air bubbles. The pieces were then washed for 30 minutes in a 1 molar solution of sodium chloride to fix the polyethyleneimine and subsequently washed thoroughly in distilled water to remove all the sodium chloride from the reactor discs. This required four washings, 50 ml and 10 minutes each. The reactor discs next were soaked in 50 cc of a 10% aqueous solution of glutaraldehyde at pH 9 and agitated frequently to ensure uniform penetration of the discs by the glutaraldehyde. After incubation in the glutaraldehyde, the discs were thoroughly washed in distilled water using four 50 ml washings for 10 minutes each. Glucose oxidase (1270 units/ml) was diluted 50/50 with phosphate buffer (0.1 molar, pH 6). The resulting solution (50 cc) was adjusted to pH 6 with dilute sodium hydroxide and the discs of Reactors Nos. 1, 2, and 3 were incubated in this solution for 30 minutes. After the 30 minute incubation, the reactor discs were removed and thoroughly washed with distilled water to remove free enzyme from the porous material, leaving behind only the immobilized enzyme.

Each of the above three reactors were assayed for activity by conversion of β-D-glucose to D-gluconolactone and monitoring the hydrogen peroxide concentration in the effluent stream. The substrate solution (β-D-glucose, 0.15 millimolar in 0.1 molar potassium phosphate buffer at pH 6) was pumped through the reactors at varying flow rates and the effluent stream collected and assayed for hydrogen peroxide which is generated according to the equation:

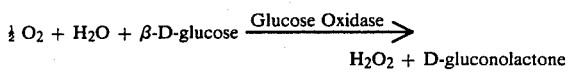

Into the analyzer cuvette is added 25 microliters of the peroxidase solution (10 mg/5 ml in potassium phosphate buffer at pH 6) and 50 microliters of reduced O-Dianisidine solution (2% in methanol). The cuvette is filled with the reactor effluent, agitated, and analyzed on a Bausch & Lomb Spectronic 20 at 460 millimicrons for optical density versus a blank standard. The observed results are summarized as follows:

Reactor No. 1

Minimum enzyme activity was exhibited by this reactor. The activity that did exist was readily washed out as the glucose solution was pumped through the reactor indicating that the enzyme was not bound to the media but rather trapped within the pores.

Reactor No. 2

This reactor exhibited good activity on the first day being almost as active as the control (Reactor No. 3) when normalized for silica content of the material. At a flow rate of 0.5 cc/min. through a 1 centimeter diameter area, the disc showed an activity of 0.65 units/gram of material. The activity seemed to drop off slightly on the second day but this was not quantified.

Reactor No. 3

This reactor exhibited good activity and revealed a constant reaction rate both days. At 0.5 cc/min. flow rate through a 1 centimeter diameter area the disc showed an activity of 1.8 units/gram of material.

It will be noted that the activity of Reactor No. 2 was approximately half that of Reactor No. 3 and also, that the material of Reactor No. 2 contained roughly half the silica filler of Reactor No. 3. This indicates that the filler (silica) constituent in the microporous material constitutes the primary binding species for the immobilized enzyme rather than the surrounding matrix, such as hard rubber or polyvinyl chloride, for example.

Although certain of the foregoing Examples illustrate the immobilized enzyme system of the present invention in the form of a so-called stacked-disc or flow-through reactor, it will be appreciated that many other forms of reactors may be employed as well. For example, the microporous starting material may be formed into the shape of a hollow tube, and treated in the manner disclosed above to bond or attach catalytically active enzymes thereto. A substrate may then be caused to flow into the tube at one end, be enzymatically reacted upon as it flows along and comes into contact with the inner wall of the tube, and the resulting product caused to flow out of the tube at its other end.

Similarly, in cases where the substrate has a relatively high viscosity, or it is otherwise desirable to utilize a packed-bed, fluidized-bed, or stirred tank type of reactor, for example, sheets of microporous starting material may have enzymes bound thereto and immobilized as above with the resulting sheets being subsequently cut-up or divided into small pieces of practically any desired size (e.g., pieces, granules, beads, powders, and so on. The resulting divided immobilized enzyme particles may then be utilized by those skilled in the art in applications requiring such forms of immobilized enzyme carrier.

Finally, as will be understood further, the immobilization principles of the present invention are applicable to proteinaceous substances other than enzymes, such as antibodies or antigens, for example. Accordingly, the present invention should be limited only by the true scope of the appended claims.

What is claimed is:

1. A method of immobilizing proteinaceous substances comprising the steps of providing an insoluble microporous member, having at least a pair of opposed surfaces and a predetermined thickness said microporous member comprising a polymeric resinous binder having finely divided filler particles dispersed throughout said binder and a network of substantially interconnected pores formed therein, said bores being formed within said resinous binder, between said filler particles and said resinous binder, and between neighboring filler particles, said dispersed filler particles being present in said microporous member in an amount by weight of at least about 25%, the size distribution of said pores varying non-uniformly across each of said surfaces and across said predetermined thickness through the range of about 0.01 micron to about 100 microns as determined porosimetrically by the Mercury Intrusion Method, and bonding a proteinaceous substance to the surface of at least some of said plurality of dispersed filler particles, said microporous member being pervious to the flow of a fluid through at least one of said surfaces wherein at least some of said filler particles to which said proteinaceous substance is bound is adapted to come into contact with such fluid.

2. The method of claim 1 wherein said proteinaceous substance is a catalytically active enzyme.

3. The method of claim 2 wherein said catalytically active enzyme is chemically bound to said surface of said filler particles by treating said support member with an intermediate coupling agent to form organic functional groups covalently bonded to said surface, and said treated support member is exposed to a solution including said enzyme to convalently bond said enzyme to said organic functional groups on the surface of said filler particles.

4. The method of claim 3 wherein said treated support member is exposed to a cross-linking agent prior to being exposed to said enzyme solution.

5. The method of claim 3 wherein said treated support member is exposed simultaneously to said enzyme solution and a cross-linking agent.

6. The method of claim 3 wherein said intermediate coupling agent is an organosilane.

7. The method of claim 6 wherein said organosilane is gamma-aminopropyltriethoxysilane.

8. The method of claim 2 wherein said catalytically active enzyme is chemically bound to said surface of said filler particles by treating said support member with an intermediate coupling agent to form organic functional groups chemiadsorbed to said surface, and said treated support member is exposed to a solution including said enzyme to covalently bond said enzyme to said organic functional groups on the surface of said filler particles.

9. The method of claim 8 wherein said treated support member is exposed to a cross-linking agent prior to being exposed to said enzyme solution.

10. The method of claim 8 wherein said treated support member is exposed simultaneously to said enzyme solution and a cross-linking agent.

11. The method of claim 8 wherein said intermediate coupling agent is a polyelectrolyte.

12. The method of claim 11 wherein said polyelectrolyte is polyethelenimine.

13. The method of claim 4 wherein said intermediate coupling agent is gamma-aminopropyltriethoxysilane and said cross-linking agent is glutaraldehyde.

14. The method of claim 5 wherein said intermediate coupling agent is gamma-aminopropyltriethoxysilane and said cross-linking agent is glutaraldehyde.

15. The method of claim 9 wherein said intermediate coupling agent is polyethelenimine and said cross-linking agent is glutaraldehyde.

16. The method of claim 10 wherein said intermediate coupling agent is polyethelenimine and said cross-linking agent is glutaraldehyde.

* * * * *